United States Patent [19]

Killion

[11] Patent Number: 4,677,679
[45] Date of Patent: Jun. 30, 1987

[54] INSERT EARPHONES FOR AUDIOMETRY

[76] Inventor: Mead C. Killion, 935 Wilshire Ave., Elk Grove Village, Ill. 60007

[21] Appl. No.: 628,009

[22] Filed: Jul. 5, 1984

[51] Int. Cl.$^4$ .......................... H04R 1/10; H04R 1/28; H04R 25/00; H03G 5/00
[52] U.S. Cl. ...................................... 381/74; 181/130; 381/103; 381/187; 381/68.6
[58] Field of Search .......................... 381/74, 87, 103; 179/179, 107 R, 180; 181/129, 130; 73/585; 455/73, 89, 90

[56] References Cited

U.S. PATENT DOCUMENTS

| 3,811,437 | 5/1974 | Gardner, Jr. | 128/152 |
| 3,930,560 | 1/1976 | Carlson et al. | 179/180 |
| 3,935,398 | 1/1976 | Carlson et al. | 179/119 A |
| 4,006,321 | 2/1977 | Carlson | 179/107 FD |

FOREIGN PATENT DOCUMENTS

| 2512343 | 10/1976 | Fed. Rep. of Germany | 179/107 R |
| 346320 | 1/1960 | Switzerland | 181/130 |

OTHER PUBLICATIONS

*Hearing Instruments,* "A New Acoustic Horn for Small Ear Canals", E. Robert Libby, vol. 3, No. 9, Sep. 1982, p. 48.

*Primary Examiner*—Gene Z. Rubinson
*Assistant Examiner*—Danita R. Byrd
*Attorney, Agent, or Firm*—Neuman, Williams, Anderson & Olson

[57] ABSTRACT

Insert earphones, which are especially useful for audiometry applications include a transducer which is coupled to a resonance cancellation tube as well as to a main tube which is coupled to the ear, with series acoustic dampers in the tubes, operating in a known manner to obtain a smoothly varying frequency response characteristic. An electrical equalization network is coupled to the transducer, cooperating with the acoustic components to obtain a frequency response characteristic which is either flat or which matches that of the human ear. The dampers in series with the main and cancellation tubes have acoustic resistances which are respectively about 20% lower and 20% higher than the characteristic impedances of such tubes, operating to obtain a broadband increase in output.

18 Claims, 10 Drawing Figures

INSERT EARPHONES FOR AUDIOMETRY

This invention relates to earphones and more particularly to earphones which have other applications and which are especially advantageous in audiometry applications. The earphones of the invention have highly accurate frequency response characteristics which extend over a wide frequency band and which are otherwise such as to permit very accurate measurements. The earphones provide a high degree of noise exclusion and are very comfortable for use over extended periods of time. They are highly reliable while being manufacturable at relatively low cost and they are also such as to attain very accurate results in auditory brainstem response (ABR) audiometry applications.

BACKGROUND OF THE INVENTION

Traditional supra-aural audiometric headphones have had several limitations.

1. Little noise exclusion at low frequencies where background noises are often a problem, when testing in schools or nursing homes, for example;

2. Poor interaural attenuation (cross-head isolation), so that a masking noise must often be used in the non-test ear;

3. A limited bandwidth (6–8 kHz), which makes reliable high-frequency audiometry difficult;

4. An inaccurate real-ear frequency response for speech, so that the spectrum of speech reproduced at the eardrum of the headphone is quite different from the spectrum that would have been produced at the eardrum by the same talker in a face-to-face situation.

5. A headband force that makes the headphones uncomfortable to wear for a long period of time and produces collapsed canals in some older individuals, giving erroneous indications of high-frequency loss. Yet this headband force is still insufficient to produce a seal, giving large test-retest variability at low frequencies.

With the advent of "objective" or ABR (Auditory Brainstem Response) audiometry, which typically uses computer averaging of the minute electrical signals that can be picked up on the head, an additional limitation became apparent:

6. The electromagnetic signal leaking from the headphone is sometimes picked up by the ABR electrodes, causing an artifact in the averaged response.

SUMMARY OF THE INVENTION

This invention was evolved with the general object of overcoming problems with prior art systems and of providing earphones which have characteristics such as to permit accurate measurements in various audiometry applications, including ABR applications, while being reliable, comfortable for the user and otherwise desirable in use.

The invention is based upon research into techniques which have been proposed for use in audiometry applications and techniques proposed for use in other applications, and research to discover the problems involved with such prior proposed techniques. The invention is also based upon the results of experiments into the performance of many different arrangements.

In the 1940's, Nobel Prize Winner Georg von Bekesy described the possibility of obtaining good noise exclusion and interaural attentuation with the use of a receiver coupled with a plastic tube to the ear. Similarly, it has been proposed that the electrical artifact problem in ABR measurements may be circumvented by using a plastic tube to couple the sound to the ear so that (a) the earphone's electromagnetic field (whose troublesome inductive component typically falls off as the cube of distance) is removed from the vicinity of the ABR electrodes and (b) the acoustic time delay gives the electromagnetic artifact time to die away before the acoustic signal (typically a click) reaches the eardrum.

There is a canal collapse problem and a discomfort problem which can be solved by sealing the tube into the ear with a soft foam earplug. In experiments, it was found that a tube with an outer diameter of 2.2 mm (0.085 inches) was about as large as could be used if the readily available foam plugs were to be squeezed down to fit all ears. This small size unfortunately reduces the practicality of "horn coupling" to improve the high-frequency response delivered to the ear, couplings that typically require inner diameters of 3 mm or more for the sound channel in the earplug, as described in several previous publications by the present writer (see, for example, the book chapter: "Problems in the application of broadband hearing aid earphones", in Acoustical Factors Affecting Hearing Aid Performance, GA Studebaker and I Hochberg (eds), [University Park Press, Baltimore, 1980]).

It was thus discovered that a particular problem can be narrowed to the attainment of a smooth, wideband frequency response at the end of a long, small diameter tube. A bandwidth of at least from 50–10000 Hz and preferably 40–15,000 Hz or better was found to be desirable. Two developments were also uncovered which might make it possible to obtain such a response: the development of wideband subminiature receivers (earphones) as exemplified by the Knowles ED-series wideband receiver, (a smaller version of the improved receiver described by Carlson, Mostardo, and Diblick in U.S. Pat. No. 3,935,398), and Carlson's elegant twin-tube damping arrangement described in his U.S. Pat. No. 4,006,321. Such developments were made for use in hearing aids but it was found that they might be modified and combined with electrical equalization in the novel manner described below, to remove most of the limitations of traditional audiometric earphones.

Figure 5:
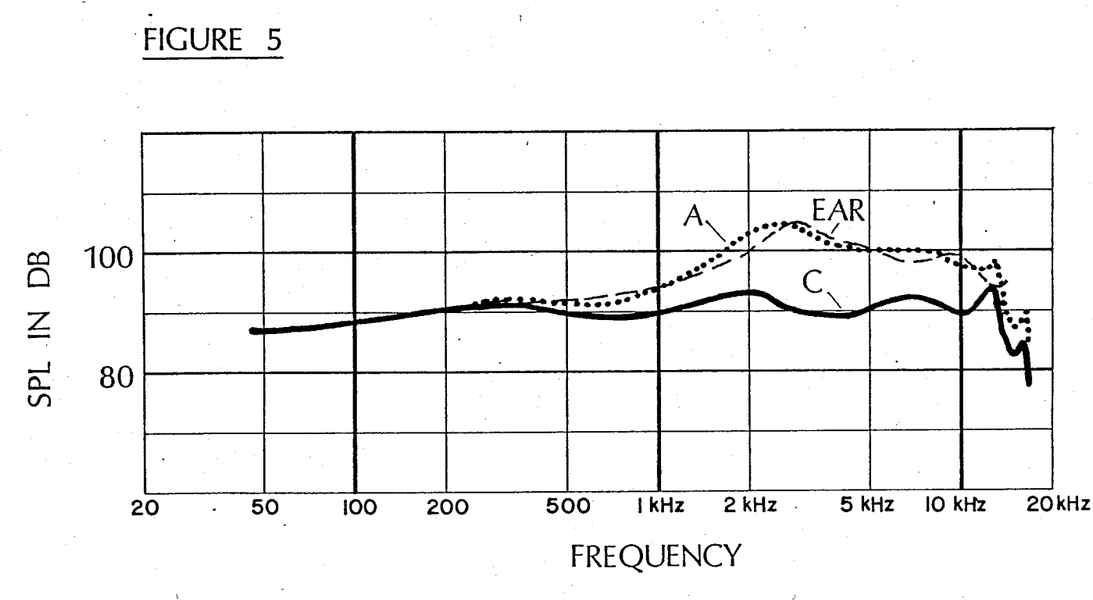
FIG. 5 illustrates the frequency response of the normal human external ear, the frequency response obtained with one network of FIG. 4 and the difference between such responses.

Two different frequency responses are useful: For speech audiometry, where the goal is to produce the same frequency response at the eardrum for speech as would be produced in the live situation, a frequency response approximately as shown in the dashed ("EAR") curve of FIG. 5 is required. This curve shows the average diffuse-field response of the normal ear, based on the data of EAG Shaw ("The acoustics of the external ear", a chapter in Acoustical Factors Affecting Hearing Aid Performance Studebaker and Hochberg(eds), 1978), GF Kuhn ("Some effects of microphone location, signal bandwidth, and incident wave field on the hearing aid input signal", a chapter in the same book), and MC Killion and EL Monser ("COR-FIG: Coupler response for flat insertion gain", another chapter in the same book). The resonances of the normal external ear ("nature's own hearing aid") must be duplicated in the earphone response if the accurate reproduction of speech (or the accurate [high-fidelity] reproduction of any normal phonograph or tape recording) is desired.

There are of course other applications for a headphone with good noise exclusion and high-fidelity sound reproduction. I have found early prototypes of the present earphones useful in making high-quality on-site recordings of music performances, where finding the correct microphone placement is traditionally an extremely time consuming task. The readily available high-accuracy headphone all provide little or no noise exclusion, so that in order to compare the live sound to the recorded sound, the recording engineer must either stop the performance in order to properly hear the playback in the same location, or else run to another location where he has monitor speakers or headphones in a soundproof environment. With noise-excluding high-fidelity earphones, however, it becomes a simple matter to make rapid A-B comparisons between the live and recorded sound (using the monitor head on the tape recorder) without leaving the performing hall.

Other applications for these earphones should be self-evident.

A different frequency response is sometimes useful for "objective" or ABR audiometry, where the accurate reproduction at the eardrum of an electrical "click" stimulus is often of interest. In this case, the desired frequency response of the sound pressure delivered to the eardrum must be flat in order that the acoustic signal at the eardrum be a close replica of the electrical signal delivered to the earphone. For example, a commonly used rectangular electrical pulse of 100 microseconds should produce an approximately rectangular pressure pulse at the eardrum without the excessive ringing that characterizes the real-ear response of many headphones.

In order to keep production costs to a minimum, it is desirable to have only one acoustic coupling configuration to serve both of the frequency response requirements described above. Accordingly, it was one object of the present invention to produce a single basic earphone design that could provide either a close replica of the normal ear's diffuse-field response to sound or an essentially flat frequency response (as measured at the eardrum in both cases), depending only on the values chosen for an electrical equalization network which might be contained in the housing for the earphone components.

Another object of the present invention was to provide a more accurate frequency response for both applications than could be obtained in commercially available noise-excluding headphones, and to provide such an accurate response when the earphone was driven by a low-impedance amplifier such as found in modern audiometers or modern high-fidelity amplifiers, which typically have an electrical output impedance of 1-2 Ohms or less.

This invention contemplates other objects, features and advantages which will become more fully apparent from the following detailed description taken in conjunction with the accompanying drawings.

DESCRIPTION OF THE PREFERRED EMBODIMENTS

Figure 1:
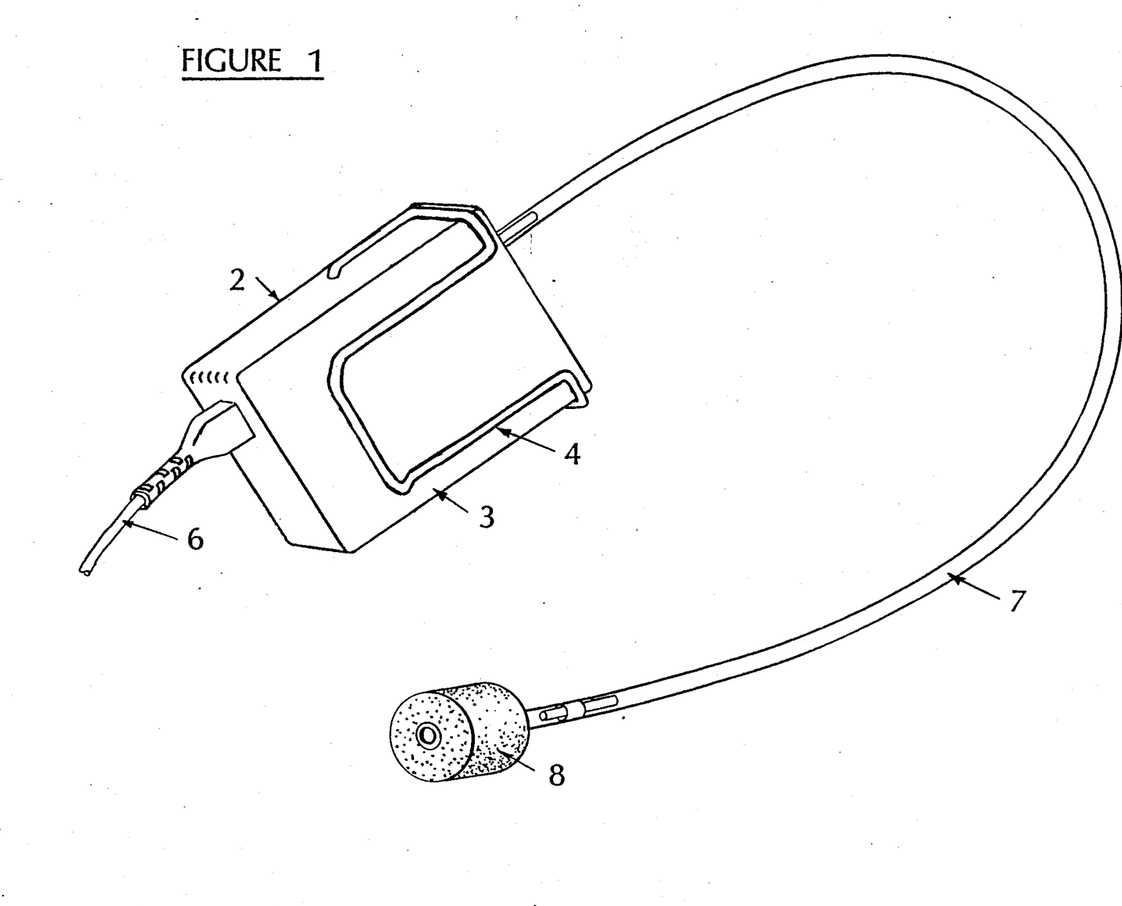
FIG. 1 is a perspective view of earphone apparatus constructed in accordance with the invention.

A preferred embodiment of the invention is illustrated in FIG. 1, including a base unit 2 which includes a rectangular case 3 and includes a clip 4 for convenient attachment to the collar of a shirt or blouse. The base unit 2 may be connected through a cable 6 to a signal generator or other source of audio signals but it will be understood that a signal generator may be incorporated within the base unit 2 to be energized by battery means within the base unit 2 or from the external supply voltage source.

The base unit 2 is connected through a main sound tube 7 to an ear piece 8 which is designed to be inserted into the end of the ear canal to position the end of the tube 7 within the ear canal.

In one preferred embodiment of the invention, the replaceable sound tube 7 has a length of 292 mm (11.5 inches) of #16 tubing (1.35 mm inside diameter), measured from the wall of the case to the tip of the earpiece 8. This length, in combination with a 13 mm length inside the case, produces an overall length of 305 mm and an acoustic time delay of 1.0 mSec; a convenient value for ABR time-base offset calibration An operating length of 305 mm is thus desirable and is made possible by this invention, but it will be understood that substantially shorter as well as longer lengths may be used without departing from the invention.

Figure 2A:
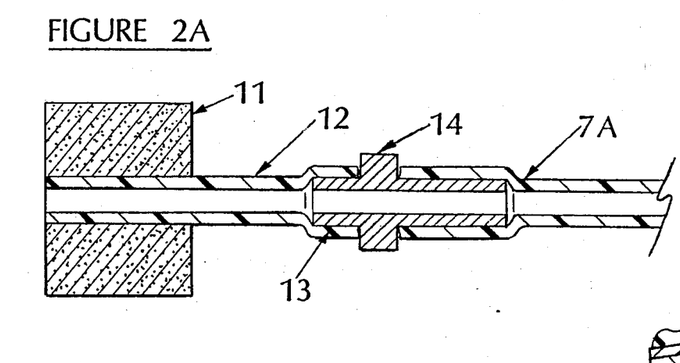
FIGS. 2A, 2B, 2C and 2D are sectional views through four earplug arrangements useable as an alternative to the ear-plug shown in FIG. 1.

The sound tube 7 is conveniently made from PVC tubing such as commonly used in hearing aid applications as a sound tube. The earplug 8 may be made from slow-recovery foam plugs attached to the PVC tubing, which was the original application shown in Gardner's U.S. Pat. No. 3,811,437 [1974] for what are now known as the "EAR" plugs widely used for hearing protection. The tube-plug combination shown in FIG. 1 is easily disposable, and may be sterilized and packaged for use in the sterile field in the surgical operating room.

Where complete sterility is not required, the alternate arrangement shown in FIG. 2A may be employed, where the disposable (although reuseable) foam plug 11 is attached to a shorter section of plastic tubing 12 into which a "socket" 13 has been molded to allow easy insertion of nipple 14 (which may be of stainless steel or other rigid material). The remainder of the sound tube 7a is precut to provide the appropriate total length for the main sound channel.

Figure 2B:
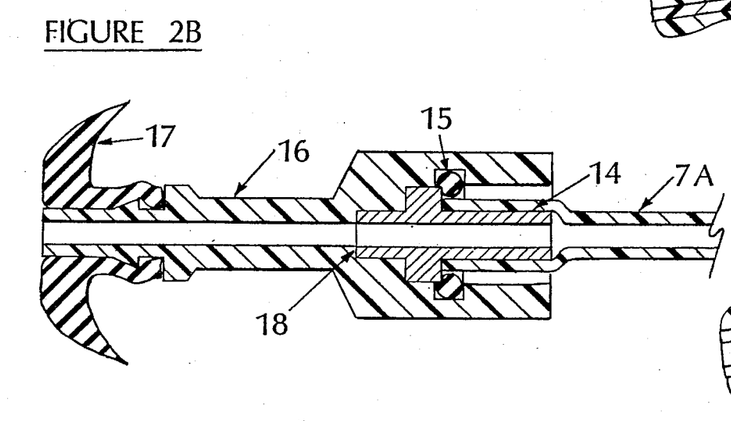

In a few cases, an unusual ear canal shape may prevent convenient sealing of the standard foam plug 8 or 11 into the ear. For those cases, an "impedance cuff" adapter 16 may be provided as shown in FIG. 2B. This allows use of any of the multi-sized rubber cuffs (ear-tips) 17 used in "impedance audiometry" to seal to the earcanal in order to allow acoustic impedance measurements to be made on virtually any ear. As shown, an O-ring 15 seals to nipple 14 and urges nipple 14 against the shoulder 18 in adapter 16, so that the same overall length of the main sound channel (from the receiver to the tip of the earpiece) is maintained (at 292 mm in the preferred embodiment).

Figure 2C:
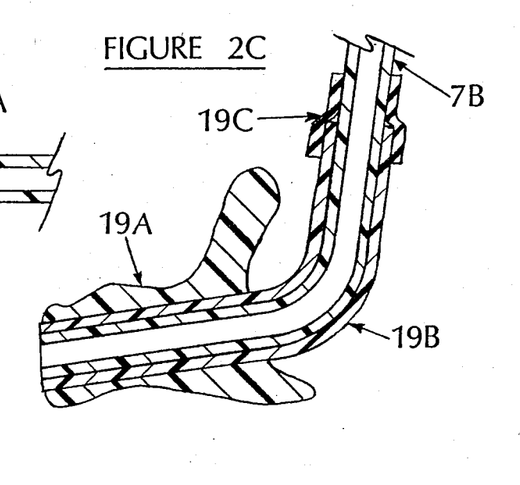
Figure 2D:
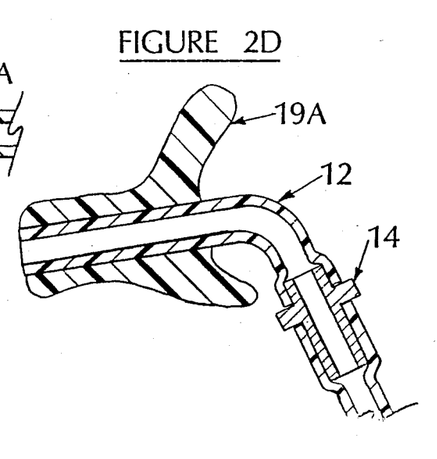

In some cases an existing earmold 19a may be available, or an instant earmold made for the purpose, using the conventional #13 hearing aid tubing 19b as shown in FIG. 2C. In this case a very-thin-wall length of (e.g. Teflon) tubing 7b may be inserted inside the #13 tubing and sealed with an elastic tubing 19c to tubing 7b. A custom earmold will often be preferred with the earphone is to be used for regular listening. For this purpose, an earmold fabricated with a 292 mm (11.5") length of #16 earmold tubing will provide the proper coupling when attached directly to the outlet nipple (27 in FIG. 3 below) of the earphone itself. Alternately, a custom earmold with a 25 mm length of #16 tubing 12 may be fabricated and nipple 14 inserted as shown in FIG. 2D.

Figure 3:
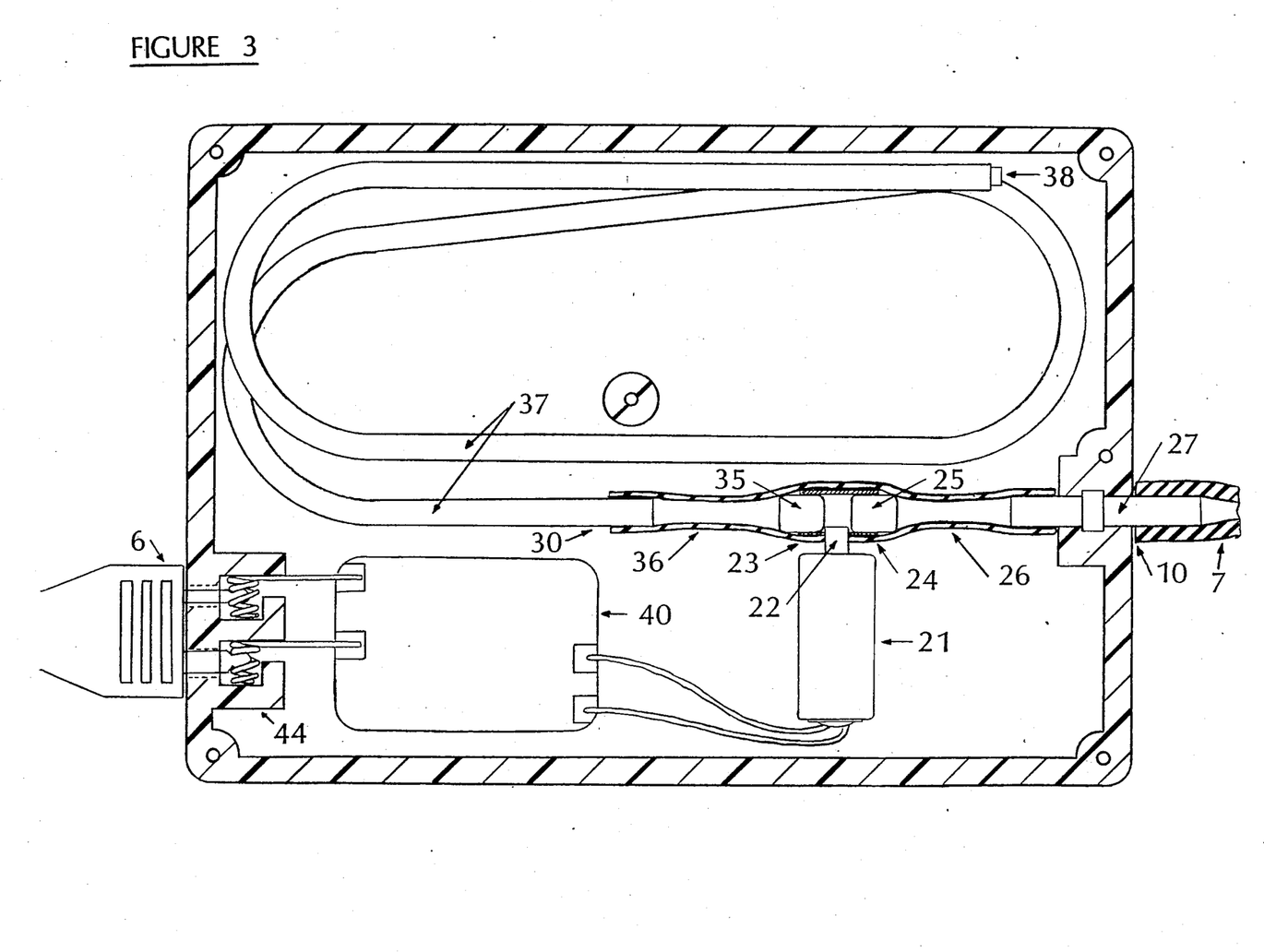
FIG. 3 is a sectional view of a base unit of the apparatus of FIG. 1.

FIG. 3 shows one preferred arrangement of the components contained in the case 3 of FIG. 1. A subminiature receiver 21, with sound outlet 22, is acoustically sealed into coupling assembly 23, which assembly contains two acoustic dampers 25 and 35 (such as, but not limited to, those dampers described by Carlson and Mostardo in U.S. Pat. No. 3,930,560), the auxiliary sound channel which I choose to call Carlson's "resonance cancellation tube" 30, consisting of a coiled tube 37 closed at the far end such as with a plug 38 and connected at the other end to coupling 23 via tube 36, a main sound channel 10 starting with tube 26 connecting coupling assembly 23 with outlet nipple 27 and continuing with sound tube 7, and an electrical equalization network 40 interposed between an electrical connector 44 and the electrical terminals of receiver 21.

In the course of my early experiments with a version having the length of the main and auxiliary sound channels set to approximately 3 inches (75 mm), I discovered that instead of following Carlson's teaching and using two equal-valued acoustic resistances chosen equal to the characteristic acoustic impedance of the sound channel tubes (approximately 41 cgs Ohms divided by the area of the tube in square centimeters, or about 2900 Ohms for 1.35 mm I.D. tubing), I could correct for a 3 dB deficiency in response near 1 kHz (approximately a quarter-wavelength for sound in a 75 mm tube) and lesser deficiency near 3 kHz (approximately $\frac{3}{4}$ wavelength) by using a value of 3300 Ohms for damper 35 (in series with the resonance cancellation tube 30) and a value of 2200 Ohms for damper 25 (in series with the main sound tube 10). I later discovered that this same combination provided a different benefit in the preferred version, which uses approximately 305 mm total length for the two sound tubes, in the form of a broadband increase in acoustic output of 1-2 dB compared to that obtained following Carlson's teaching, while still maintaining the smooth frequency response that is the principal benefit of his approach.

Figure 4:
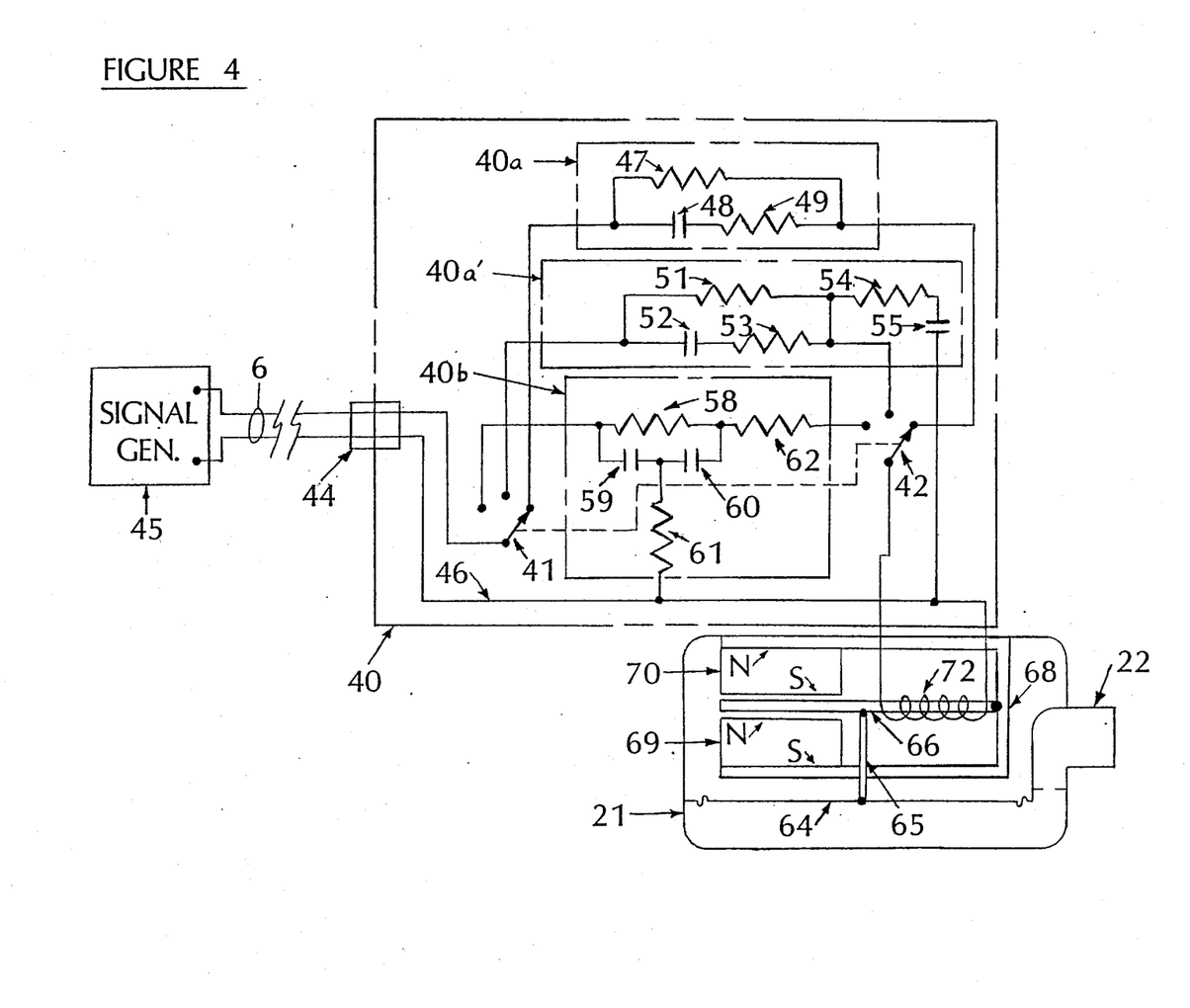
FIG. 4 illustrates the circuit of an electrical response-equalization network circuit of the apparatus and also illustrates diagrammatically the construction of a transducer of the apparatus.

As shown in FIG. 4, the equalization network circuit 40 includes three selectively useable networks 40a, 40a' and 40b, networks 40a and 40b being basic types of networks and network 40a' being a modification of network 40a. In the arrangement as illustrated, ganged selector switch contacts 41 and 42 are selectively connectable to input and output terminals of the three networks. Contact 41 is connected to a terminal of a connector 44 which is connected through one conductor of the cable 6 to one output terminal of a signal generator 45. Contact 42 is connected to one terminal of the transducer 21. A common line 46 is connected to the other terminal of transducer 21 and to a second terminal of connector 44 which is connected through a conductor of cable 6 to a second output terminal of the signal generator 45.

It will be understood that in apparatus intended for one particular type of application only one of the networks may be required. As aforementioned, the signal generator 45 may be incorporated in the base unit 2. It may be energized from a battery within the base unit 2 or from an external voltage supply, through cable 6.

Network 40a includes a resistor 47 in series between input and output terminals and a capacitor 48 in parallel relation to the resistor 47. An additional resistor 49 is shown in series with capacitor 48, but may not be required in certain cases, i.e. its resistance may be zero. Network 40a' includes a resistor 51, a capacitor 52 and a resistor 53 similar to resistor 47, capacitor 48 and resistor 49 and, in addition, includes a resistor 54 in series with a capacitor 55 and connected between the output terminals.

Network 40b includes a series resistor 58, similar to resistors 47 and 51 and a pair of capacitors 59 and 60 which are connected in series with each other and in parallel with resistor 58. The junction between capacitors 59 and 60 is connected through a resistor 61 to the common line 46, a bridged-T section being formed. An additional resistor 62 is illustrated, in series between the output of the bridged-T section and the transducer 21.

As diagrammatically illustrated, the transducer 21 includes a diaphragm 64 which defines one wall of a chamber 65 coupled to the sound outlet 22. A central portion of diaphragm 64 is coupled through a link 65 to an armature 66 of magnetic material which has a fulcrum end supported by a bight portion of a U-shaped magnetic yoke 68 with permanent magnets 69 and 70 secured to legs of the yoke 68 and defining an air gap in which a free end portion of the armature 66 is movable. Armature 66 extends through a coil 72, disposed between the fulcrum point and the magnets 69 and 70. It will be understood that other types of transducers may be used.

Curve A in FIG. 5 shows the frequency response produced when network 40a is used, with 0.316 VAC electrical input and with the output of the earphone measured in a "Zwislocki coupler" (more formally designated as an Occluded Ear Simulator, as described in American National Standard S3.25-1979, American National Standards Institute, New York, NY). Curve C in FIG. 3 shows the difference between the earphone response and the normal ear response shown as Curve EAR, and thus Curve C represents as estimate of the accuracy (fidelity) with which the subject earphone reproduces typical pre-recorded material for the idealized "average listener" when used with network 40a.

Figure 6:
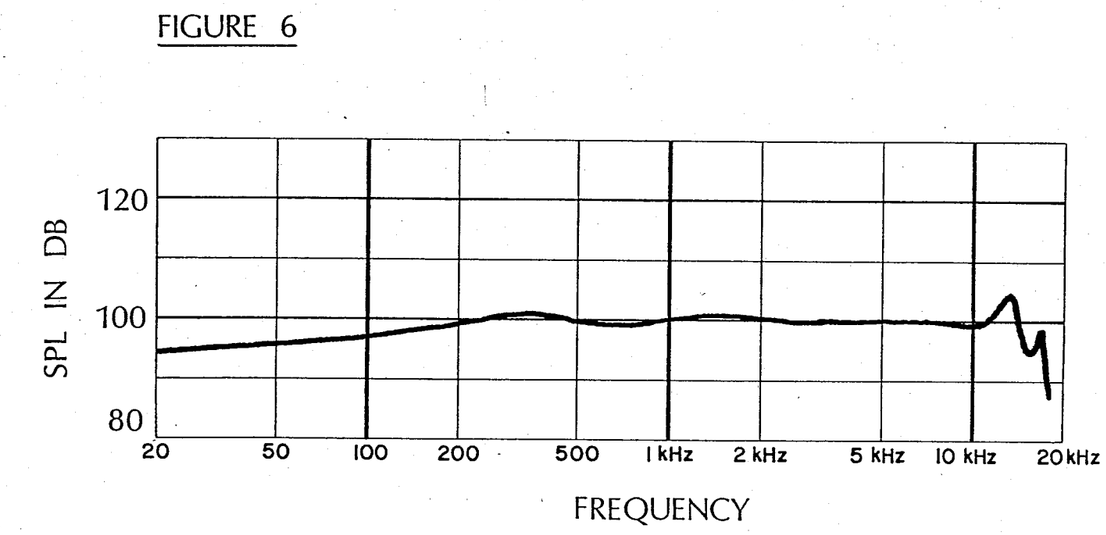
FIG. 6 shows the frequency response obtained with another network of FIG. 4.

FIG. 6 shows the frequence response, measured in the Zwislocki coupler, that obtains with 1 VAC input when network 40b is used. Note that this response would not be a good response for reproducing normally recorded speech (or music), which would sound quite dull due to the lack of the normal high-frequency boost our external ears normally provide. (The response of FIG. 6 would be quite appropriate, however, for reproducing sounds recorded with a probe microphone at the eardrum of a subject, or for sounds recorded at the eardrum-position microphone of the "KEMAR" manikin.) When driven with a 100 microsecond rectangular electrical pulse, the earphone with network 40b will produce a roughly rectangular pressure pulse at the eardrum, without excessive ringing, with linear (unchanged waveform) operation to 110 dB SPL peaks measured in the Zwislocki coupler.

The design of the equalization networks will be best understood from examples of networks which have been constructed and used in conjunction with particular types of receivers or transducers, and with tubing and other acoustic components having configurations as illustrated and having dimensions as described above. The principles outlined in the following examples can be applied to systems using transducers having different characteristics from those of the examples and/or using acoustic components with forms or dimensions different from those of the examples.

Figure 7:
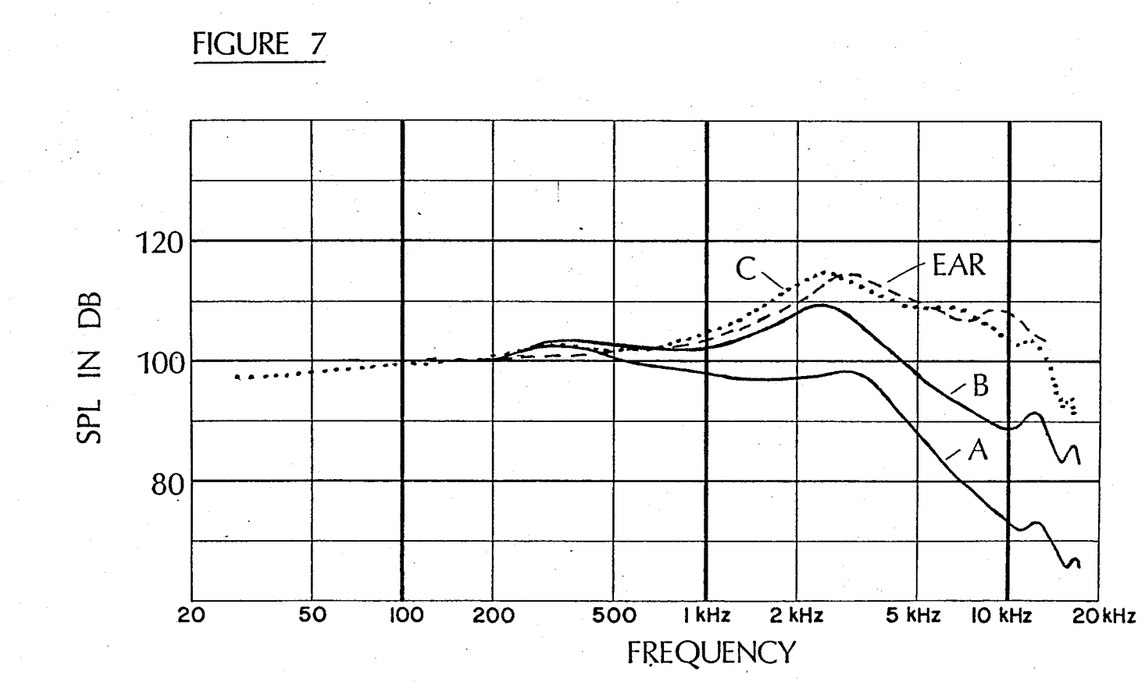
FIG. 7 illustrates the frequency responses obtained with various energization arrangements as compared with the response of the normal human external ear, for explanation of the design and operation of the networks used in the apparatus of the invention.

Curve A in FIG. 7 shows the constant-voltage response of a popular Knowles ED-1932 receiver, used here for sake of illustration, when driven with 0.2 VAC and acoustically coupled as shown in FIGS. 1 and 2. This receiver, the lowest-impedance receiver commonly sold in this series, has a DC resistance of approximately 200 Ohms and an AC impedance of approximately 700 Ohms at 1000 Hz due to its substantially inductive impedance at high frequencies. While the 0.2 VAC drive inadequate to drive the receiver to near overload at low frequencies, the receiver response at 10 kHz is some 25 dB below its response at 100 Hz. This is nearly 35 dB below the response required to match the normal ear's increase of approximately 10 dB at 10 kHz compared to 100 Hz (shown here and previously in FIG. 5 as Curve "EAR").

A common way to improve the relative high-frequency response of subminiature receivers is to use a "constant current" source drive and perhaps to add a small capacitor in shunt with the receiver terminals (see the "Problems..." chapter mentioned above). Curve B in FIG. 7 illustrates the effect of placing a 7000 Ohm resistance (approximately 10 times the nominal impedance of the receiver) in series with the electrical terminals of the receiver and increasing the drive voltage to 5 VAC. Curve C in FIG. 7 shows the effect of adding a 0.012 microFarad capacitor in shunt with the 7000 Ohm constant-current resistor (note that the capacitor is not in shunt with the receiver terminals as sometimes recommended).

The response shown in Curve C of FIG. 7 is a reasonable approximation to the desired response shown as Curve EAR. The deficiency in response at 10 kKz can be solved by further refinement in the choice of R and C: The value of C shown here produces a maximum boost due to the resonance of the receiver inductance with the Capacitor C at approximately 5 kHz. A somewhat lower value of capacitance, coupled with a correspondingly higher value for R in order to maintain the same basic response shape below 5 kKz, can result in the more accurate response shown in FIG. 3.

The remaining problem is that some audiometers can not supply 5 V AC drive, having been designed to use 10 Ohm headphones with an acoustic output of approximately 120 dB or more for 1 V drive. This problem can be solved, however, by obtaining specially wound low-impedance subminiature earphones. The receivers used in the preferred embodiment, for example, have a nominal impedance of about 10 Ohms, some 50 times lower than the typical hearing-aid receiver, providing approximately a seven-fold increase in voltage sensitivity.

The electrical equalization network 40a shown in FIG. 4 shows one set of values with which the response curve A of FIG. 5 can be obtained using the preferred low-impedance receivers. The alternate network 40a' shown in FIG. 4 has the advantage that variations in receiver characteristics can be accommodated in order that all finished earphones have essentially the same sensitivity and frequency response. By varying the ratio of the capacitances of capacitators 52 and 55, the response in the 4-8 kHz region (approximately) can be controlled relatively independently of the rest of the curve. By varying the value of capacitor 55, on the other hand, the response in the 10-12 kHz region can be more or less independently controlled. And by choosing the value of resistor 51, the low-frequency sensitivity may be more or less independently controlled.

A different form of electrical equalization network is required in order to produce a relatively flat eardrum-pressure frequency response curve. I have found that the "Bridged-T" network 40b may be used to adjust the high-frequency response (controlled primarily by the series capacitors 59 and 60) to be equal to the low frequency response (controlled primarily by resistor 58), and remove the response boost at 2500 Hz, whose height after equalization is controlled primarily by the value of resistor 61. The frequency response shown in FIG. 6 was obtained with 1 VAC input to network 40b connected to the preferred low-impedance receiver, whose output was coupled as shown in FIGS. 1 and 2 and measured in a Zwislocki coupler.

It is noted that the resistance of interconnecting cables and the internal impedance of the signal generator, or other audio signal soure which is used, may be significant and should be taken into account in the choice of component values.

The frequency responses shown in FIGS. 5 and 6 have an accuracy unequalled, to my knowledge, in any commercially available noise-excluding earphone intended for either application.

By way of example and not by way of limitation, the values of the components of the illustrated circuits may be as follows:

| Reference Numeral | Value |
| --- | --- |
| 47 | 160 ohms |
| 48 | 0.68 microfarads |
| 49 | 0. ohms |
| 51 | 200 ohms |
| 52 | 0.56 microfarads |
| 53 | 0 ohms |
| 54 | 22 ohms |
| 55 | 0.27 microfarads |
| 58 | 200 ohms |
| 59 | 1.2 microfarads |
| 60 | 1.2 microfarads |
| 61 | 14 ohms |
| 62 | 20 ohms |

It will be understood that modifications and variations may be effected without departing from the novel concepts of the invention.

What is claimed is:

1. An insert earphone apparatus including transducer means positionable away from the entrance of the human ear, and sound transmission means for transmitting sound from said transducer means to a point at the eardrum, said sound transmission means including a main sound transmission tube, first coupling means between said transducer means and one end of said tube, second coupling means at the opposite end of said tube and arranged for transmission of sound from said tube through an earpiece to said point at the eardrum, said earpiece substantially preventing exterior sounds from reaching the eardrum, and acoustic response-modifying means including damping means operative to negate the effect of resonances in said tube and to otherwise modify the acoustic response characteristic from that which would be produced by said tube and coupling means alone and thus producing a smoothly varying acoustic response characteristic, an electrical response-equalization network having an input for coupling to a signal source and an output coupled to said transducer means and having an electrical response characteristic, wherein said electrical response characteristic and said smoothly varying acoustic frequency response characteristic produce a sound pressure level at the eardrum which is a function of frequency according to one of first and second frequency response characteristics depending only upon component values in said electrical equalization network, said first frequency response characteristic being a substantially flat response characteristic, and said second frequency response characteristic being such as to closely match the diffuse-sound-field response of the normal human external ear.

2. An apparatus as defined in claim 1, wherein said acoustic response-modifying means includes resonance cancellation means comprising means defining a narrow elongated cancellation channel having an open entrance end and an opposite closed end, said first coupling means being arranged to define a coupling chamber coupled to said transducer means and in closely coupled relation to said open entrance end of said cancellation channel and said one end of said main sound transmission tube, and acoustic damper means for damping transmission in said cancellation channel and said main sound transmission tube, said main sound transmission tube and said cancellation channel having substantially the same lengths.

3. An apparatus as defined in claim 2, wherein said acoustic damper means includes a first acoustic damper in series with said main sound transmission tube and a second acoustic damper in series with said cancellation channel, said first damper having an acoustic resistance which is approximately 20% less than the characteristic acoustic impedance of said main sound transmission tube, and said second damper having an acoustic resistance which is approximately 20% greater than the characteristic acoustic impedance of said cancellation channel, in order to effect a smooth frequency response with a broadband increase in output over that obtainable with dampers whose resistances are equal to the characteristic impedances of said tube and said cancellation channel.

4. An apparatus as defined in claim 1, said network means including impedance means having a value changing with frequency to compensate for variations with frequency in the effective impedance and effective efficiency of said transducer means and to compensate for losses in transmission of energy in said main channel which increase with frequency.

5. An apparatus as defined in claim 4, signal generating means for supplying an electrical signal for drive of said transducer means, said network means including capacitor means connected in series relation between said signal means and said transducer means for reducing the series impedance therebetween and increasing the drive of said transducer means as a function of increasing frequency.

6. An apparatus as defined in claim 5, said transducer means including diaphragm means and coil means energizeable to effect vibration of said diaphragm means, said network further including resistance means connected in series between said signal means and said coil means of said transducer means and in parallel relation to said capacitor means.

7. An apparatus as defined in claim 6, said transducer means having a certain nominal electrical impedance, said resistance means having a resistance several times larger than said nominal impedance of said transducer means, and said capacitor means having an impedance at 1000 Hz of about the same order of magnitude as the resistance of said resistance means.

8. An apparatus as defined in claim 7, said one of said frequency response characteristics being said first frequency response characteristic which is substantially flat over said range, said capacitance means comprising a pair of capacitors connected in series with each other and in series between one terminal of said signal means and one terminal of said coil means, said signal and coil means having interconnected second terminals, said network further including an additional resistance means connected between the junction between said capacitors and said interconnected second terminals of said signal and coil means.

9. An apparatus as defined in claim 8, said network further including another resistance means connected in series with the parallel combination of the first-mentioned resistance means and said pair of series-connected capacitors.

10. An apparatus as defined in claim 7, said one of said first and second frequency response characteristics being said second frequency response characteristic which closely matches the characteristic of the normal human ear, said network further including second capacitance means and second resistance means connected in series with each other to form a series circuit connected in parallel relation to said coil means.

11. An earphone apparatus including transducer means positionable away from the entrance of the human ear and sound transmission means for transmitting sound from said transducer means to a point at the eardrum, said apparatus being arranged to operate over a frequency range extending from less than 50 Hz to more than 10,000 Hz and to produce a sound pressure level at the eardrum which is a predetermined function of frequency, said sound transmission means comprising: main channel means defining a narrow elongated main channel having an open entrance end and having an open exit end for positioning within the ear canal, resonance cancellation means including means defining a narrow elongated cancellation channel having an open entrance end and an opposite closed end, means defining a coupling chamber coupled to said transducer means and in closely coupled relation to said open entrance ends of said main and cancellation channels, and acoustic damper means for damping transmission in said channels, said acoustic damper means including a first acoustic damper in series with said main channel and a second acoustic damper in series with said cancellation channel, said first damper having an acoustic resistance which is approximately 20% less than the characteristic acoustic impedance of said main channel, and said second damper having an acoustic resistance which is approximately 20% greater than the characteristic acoustic impedance of said cancellation channel, in order to effect a smooth frequency response with a broadband increase in output over that obtainable with dampers whose resistances are equal to the characteristic impedances of the two said channels.

12. An apparatus as defined in claim 11, wherein said main and cancellation channels have inside diameters of about 1.35 mm to provide characteristic impedances or both channels of about 2900 acoustic ohms and wherein the acoustic resistance of said first damper is about 2200 ohms and the acoustic resistance of said second damper is about 3300 ohms.

13. An apparatus as defined in claim 11, said main channel means comprising ear plug means arranged for positioning said exit end of said main channel within the entrance opening of the ear canal and arranged for providing a seal with respect to external sounds.

14. An apparatus as defined in claim 13, said main channel means further including an elongated flexible tube, a support tube of short length carrying said ear plug means, and connector means between one end of said flexible tube and said support tube.

15. An apparatus as defined in claim 14, said connector comprising a nipple having one end portion within said one end of said flexible tube and having an opposite end portion within one end of said support tube.

16. An apparatus as defined in claim 15, said resonance cancellation channel means comprising an elongated tupe coiled within said housing means.

17. An apparatus as defined in claim 13, said main channel means further including an elongated flexible tube connected at one end to said ear plug means, housing means enclosing said electrical response-equalization network, said transducer means, said coupling chamber means and said resonance cancellation channel means, and means for coupling an opposite end of said flexible tube to said coupling chamber means within said housing means.

18. An apparatus as defined in claim 11, said transducer means comprising a vibratory diaphragm in closely coupled relation to said coupling chamber.

* * * * *

UNITED STATES PATENT AND TRADEMARK OFFICE
CERTIFICATE OF CORRECTION

PATENT NO. : 4,677,679
DATED : June 30, 1987
INVENTOR(S) : MEAD C. KILLION

It is certified that error appears in the above-identified patent and that said Letters Patent is hereby corrected as shown below:

Column 1, line 31, delete "of" and insert -- by --.

Column 5, line 11, delete "with and insert -- when --.

Column 6, line 53, delete "as" and insert -- an --.

Column 7, line 26, delete "inadequate" and insert -- is adequate --.

Column 7, line 50, "kKz" should be "kHz".

Column 7, line 57, "kKz" should be "kHz".

Column 12, claim 16, line 9, delete "tupe" and insert -- tube --.

Signed and Sealed this

Fifth Day of January, 1988

*Attest:*

DONALD J. QUIGG

*Attesting Officer*  *Commissioner of Patents and Trademarks*